US005554513A

United States Patent [19]
Revel et al.

[11] Patent Number: 5,554,513
[45] Date of Patent: Sep. 10, 1996

[54] PRODUCTION OF RECOMBINANT HUMAN INTERFERON-BETA$_2$

[75] Inventors: Michel Revel; Asher Zilberstein, both of Rehovot, Israel

[73] Assignee: Yeda Research & Development Co. Ltd., Rehovot, Israel

[21] Appl. No.: 449,447

[22] Filed: Dec. 12, 1989

Related U.S. Application Data

[63] Continuation of Ser. No. 860,883, May 8, 1986, abandoned, which is a continuation-in-part of Ser. No. 208,925, Nov. 20, 1980, Pat. No. 5,468,607.

[30] Foreign Application Priority Data

Nov. 21, 1979 [IL] Israel .......................................... 58765
Oct. 14, 1985 [IL] Israel .......................................... 76714

[51] Int. Cl.$^6$ .......................... C12P 21/04; C12N 15/00; C12N 15/22
[52] U.S. Cl. .................................. 435/69.51; 435/240.2; 435/243; 435/252.3; 435/320.1; 536/23.52
[58] Field of Search ................................... 435/69.51, 91, 435/172.3, 240.2, 252.3–252.35, 320.1; 536/27, 23.52; 935/11, 29, 34, 70–75

[56] References Cited

FOREIGN PATENT DOCUMENTS

| | | | |
|---|---|---|---|
| 0028033 | 5/1981 | European Pat. Off. | 435/172.3 |
| 0041767 | 12/1981 | European Pat. Off. | 435/172.3 |
| 0041313 | 12/1981 | European Pat. Off. | 435/172.3 |
| 0257406 | 3/1988 | European Pat. Off. | |
| 2063882 | 6/1981 | United Kingdom | 435/172.3 |
| 88/00206 | 1/1988 | WIPO | |

OTHER PUBLICATIONS

M. Revel et al, "Expression of human IFN–$\beta_2$ and type I IFN–receptor genes in rodent cells"; Abstracts: The 1985 TNO–ISIR meeting on the Interferon System Clearwater, 13–18 Oct. 1985, p. 4.

M. Revel et al, "Expression of human IFN–$\beta_2$ genes in rodent cells"; 1986 Elsevier Science Publishers B.V. (Biomedical Division), The Biology of the Interferon System 1985, W. E. Stewart II and H. Schellekens, editors; pp. 207–216.

Sehgal, P. B. et al., "Detection of Human Beta–2 Interferon Using a Radioimmunoassay," *Journal of Interferon Research*, vol. 14, No. 1 (1984), pp. 63–66.

Sehgal, P. B. et al., "Detection of Human Beta–2 Interferon Using a Radioimmunoassay," *J. Interferon Res.*, vol. 4, No. 1, pp. 63–66 (1984).

Hirano, T. et al., "Complementary DNA For a Novel Human Interleukin (BSF–2) That Induces B Lymphocytes to Produce Immunoglobulin," *Nature*, vol. 324, pp. 73–76 (1986).

Hirano, T. et al., "Purification to Homogeneity and Characterization of Human B–cell Differentiation Factor (BCDF or BSFp–2)", *Proc. Natl. Acad. Sci. USA*, vol. 82, pp. 5490–5494.

Haegeman, G. et al "Structural analysis of the sequence coding for an inducible 26–kDa protein in human fibroblasts", European Journal of Biochemistry, vol. 159(3):625–632 (Sep. 1986).

Patent Abstracts of Japan, vol. 10 No. 13 (C–323) (2070) Jan. 18, 1986; JP–A–60 169 424 (Kishimoto Chiyuuzou et al), Sep. 2, 1985.

Patent Abstracts of Japan, vol. 11, No. 96 (C–412) (2543) Mar. 26, 1987; JP–A–61 246 197 (Ajinomoto Co., Inc.) Nov. 1, 1986.

Maroteaux et al; The EMBO Journal 2: 325 (1983).

Green et al; *Cell Shape and Surface Architecture*, 1977, Alan R. Liss, Inc., New York, pp. 493–500 reprinted in *Readings in Mammalian Cell Culture* (second edition), 1981, Pollack (ed.), Cold Spring Harbor Laboratory, Cold Spring Harbor, NY, pp. 149–156.

Weiss et al; Proc. Natl. Acad. Sci. USA 58: 1104 (1967).

Roberts et al; Proc. Natl. Acad. Sci. USA 76: 760 (1979).

Brennand et al; J. Biol. Chem. 258: 9593 (1983).

E. Knight et al, "Human Fibroblast Interferon: Amino Acid Analysis and Amino Terminal Amino Acid Sequence", (1980), *Scence*, 207, 525–526.

Y. Mory et al, "Synthesis of Human Interferon $\beta_1$ in Escherichia coli Infected by a Lambda Phage Recombinant Containing a Human Genomic Fragment", (1981), *Eur. J. Biochem.* 120:197–202.

Revel, M. et al., "Genetic and Functional Diversity of Interferons in Man", (1983), *Interferon*, v.5 p. 205–239.

D. Novick et al, "Affinity Chromatography of Human Fibroblast Interferon (IFN–B$_1$) by Monoclonal Antibody Columns", (1983), *J. Gen. Virol.*, 64:905–910.

U. Nir et al, "A Human IFN–B$_1$ gene deleted of promoter sequences upstream from the TATA box is controlled post––transcriptionally by dsRNA", (1984), *Nucl. Acids Res.* 12:6979–6993.

Y. Chernajovsky, et al, "Efficient Constitutive Production of Human Fibroblast Interferon by Hamster Cells Transformed with the IFN–$\beta_1$ Gene Fused to An SV 40 Early Promoter", (1984), *DNA* 3:297 and 299–308 only.

J. Content, et al, "Introduction of a 26–kDa–protein mRNA in human cells treated with an interleukin–1–related, leukocyte–derived factor", (1985), *Eur. J. Biochem.* 152:253–7.

(List continued on next page.)

*Primary Examiner*—James Martinell
*Attorney, Agent, or Firm*—Browdy and Neimark

[57] ABSTRACT

Human interferon-beta$_{2_A}$ and interferon-beta$_{2_B}$ are produced in purified form by recombinant DNA techniques. Two separate human genes have been identified which code for the production of IFN–$\beta_{2_A}$ and IFN–$\beta_{2_B}$, respectively. The sequence of IFN–$\beta_{2_A}$ cDNA is established. These genes and cDNA have been cloned into mammalian cells with an SV40 early promoter sequence and such genomic clones are capable of producing IFN–$\beta_{2_A}$ and IFN–$\beta_{2_B}$. The anti-viral activity of such recombinant IFN–$\beta_{2_A}$ and IFN–$\beta_{2_B}$ is demonstrated as well as other biological activity identifying them as human interferons.

24 Claims, 5 Drawing Sheets

OTHER PUBLICATIONS

J. Weissenbach, et al, "Two interferon mRNAs in human fibroblasts: In vitro translation and Escherichia coli cloning studies", (1980), *Proc. Natl. Acad. Sciences USA* 77:7152–7156.

A. Zilberstein, et al, "Structure and expression of cDNA and genes for human interferon–beta–2, a distinct species inducible by growth–simuatory cytokines", (1986), *The EMBO Journal* vol. 5 No. 10 pp. 2529–2537.

A. Zilberstein, et al "Human Interferon–Beta–2: Is it an Interferon–inducer?", The IFN System, Ed. F. Dianzani et al, Serono Symposia, Publications vol. 24, Rome, (1985).

J. Weissenbach, et al, "Identification of the Translation Products of Human Fibroblast Interferon mRNA in Reticulocyte Lysates", *Eur. J. Biochem.*, (1979) 98, 1–8.

M. Revel, et al "Interferon–Induced Enzymes: Microassays and Their Applications; Purification and Assay of (2'–5')–Oligoadenylate Synthetase and Assay of 2'–Phosphodiesterase", (1981), *Meth. Enzymol.*, vol. 79, 149–161.

FIG.1  IFN-β2a cDNA

FIG. 4

IFN-β2 Gene, Clone IFA-2

```
        -150       -140       -130       -120       -110       -100
IFA-2   ACTAAAGGACGTCACATTGCACAATCTTAATAAGGTTTCCAATCAGCCCCACCCGCTCTG

-90        -80        -70        -60        -50        -40
IFA-2   GCCCCACCCTCACCCTCCAACAAAGATTTATCAAATGTGGGATTTTCCCATGAGTCTCAA

-30        -20        -10         1         10         20
IFA-2   TATTAGAGTCTCAACCCCCAATAAATATAGGACTGGAGATGTCTGAGGCTCATTCTGCCC
cDNA    *****               ******        -------...-----------ATTCTGCCC
        TATA-1              TATA-2       S-1                    S-2

30xhol     40         50         60         70         80
IFA-2   TCGAGCCCACCGGGA-CGAAAGAGAAGCTCGATCTCCCCTCCAGGAGCCCAGCTATGAAC
cDNA    TCGAGCCCACCGGGAACGAAAGAGAAGCTCTATCTCCCCTCCAGGAGCCCAGCTATGAAC
                                                                  X 90         100   intr1 110        120        130        140
IFA-2   TCCTTCTCCACAA GTAAGTGCAGGAAATCCTTAGCCCTGAACTGCCAGCGGGGTCGAGCC
cDNA    TCCTTCTCCACAA GCGCCTTCGCTCCAGTTGCCTTCTCCCTGGGGCTGCTC....

150        160        170        180        190        200
IFA-2   CTGTGTGAGGGAGGGGTGTGTGGCCCAAGGAGGGCTGGCGGGCGGCCAGCAGCAGAGGCA 210        220        230        240        250
IFA-2   GGCTCCCAGCTGTGCTGTCAGCTCACCCTGCGCTCGCTCCCTCGC....
```

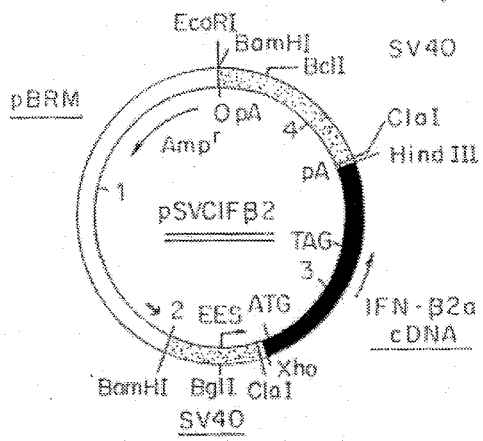
FIG. 5 CONSTITUTIVE EXPRESSION OF HuIFN β2 IN CHO CELLS
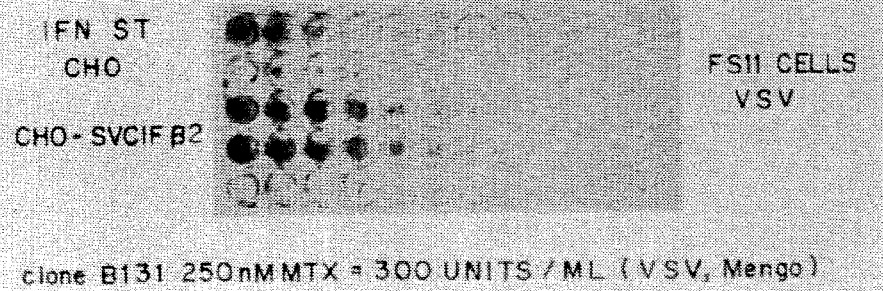
clone B131 250nM MTX = 300 UNITS/ML (VSV, Mengo)
FIG. 6 INDUCTION OF 2'-5' OLIGO A SYNTHETASE BY r-IFN-β2 FROM GENE TRANSFECTED CELLS
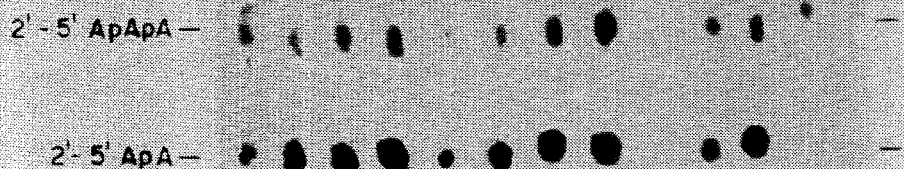

CONSERVED AMINOACIDS IN HUMAN TYPE I IFNs COMPARED TO IFN-2 SEQUENCE

```
                                                                         MNSFS
                                                      oo  o  o   1     o
IFN β-2     TSAFGPVAFSLGLLLVLPAAFPAPVPPGEDSKDVAAPHRQPLTSSERIDKQIRYILDGIS
                                                      -21
IFN β-1                                 MTNKCLLQIALLLCFSTTALS
                                          -23
IFN α-A                                 MALTFALLVALVVLSCKSSCS
IFN α-C                                 MALSFSLIMAVIVLSYKSICS
IFN α-II                                MVLLIPLLVALPLCHCGPVGS o       *o     o    **   *    *o  o
IFN β-2     ALRKETCNKSNMCESSKEALAENNLNLPKMAEKD-GCFQSGFNEETCLVKIITGL
            1    *           *      *****       *       *  **
IFN β-1     MSYNLLGFLQRSSNFQCQKLLWQINGRLEYCLKDRMNFDIPE-FIKQLQQFQKED
            1
IFN α-A     VGCDLPQTHSLGSRRTLMLLAQMRKISLFSCLKDRHDFGFPQ-EEF-GNQFQKAE
IFN α-C     LGCDLPQTHSLGNRRALILLGQMGRISPFSCLKDRHDFRIPQ-EEFDGNQFQKAQ
              N SE   D     M    S    S   M    E QP     DK     P
IFN α-II    LSCDLPQNHGLLSRNTLVLLHQMRRISPFLCLKDRRDFRFPQ-EMVKGSQLQKAH o * o*o *         **                *
IFN β-2     LEFEVYLEYLQNRF------ESSEEQARAVQMSTKVLIQFLQKKAKNLDAI-----
                *  *   *  *    **              *
IFN β-1     AALTTY-EMLQNIFAIFRQDSSTGWNETIVENLLANVYH-QINHLKTVLEEKLEK

IFN α-A     TIPVLH-EMIQQIFNLFSTKDSSAAWDETLLDKFYTELYQ-QLNDLEACVIQEVGV
IFN α-C     AISVLH-EMIQQTFNLFSTEDSSAAWEQSLLEKFSTELYQ-QLNDLEACVIQGVGV
              IM     T  N    TL D    CI D     M     VLCD  FR
IFN α-II    VMSVLH-EMLQQIFSLFHTERSSAAWNMTLLDQLHTELHQ-QLQHLETCLLQVVGE oo     o*              *       *    *o*oo     oo o**
IFN β-2     -TTPDPTTNASLLT-----------KLQAQNQWLQDMTTHLILRSFKEF--LQSSLRALRQM#
                  *     *  **  * **  ***  **    ** *              **
IFN β-1     EDFTRGKLMSSLHLKAYYGAILHYLRAKEYSHCAWTIVRV--EILRHFYFINALTGYLRN#

IFN α-A     TETPLMKEDSILAVRKYFQRITLYLKEKKYSPCAWEVVRA--EIMRSFSLSTNLQESLASKE#
IFN α-C     EETPLMNEDSILAVRKYFQRITLYLIERKYSPCAWEVVRA--EIMRSLSFSTNLQKRLRRKD#
              IS    YV    K   R    T   S                      IIF
IFN α-II    GFSAGAISSPALTLRRYFQGIRVYLKEKKYSDCAWEVVRM--EIMKSLFLSTNMQERLRSKDRDLGSS#
```

FIG. 7

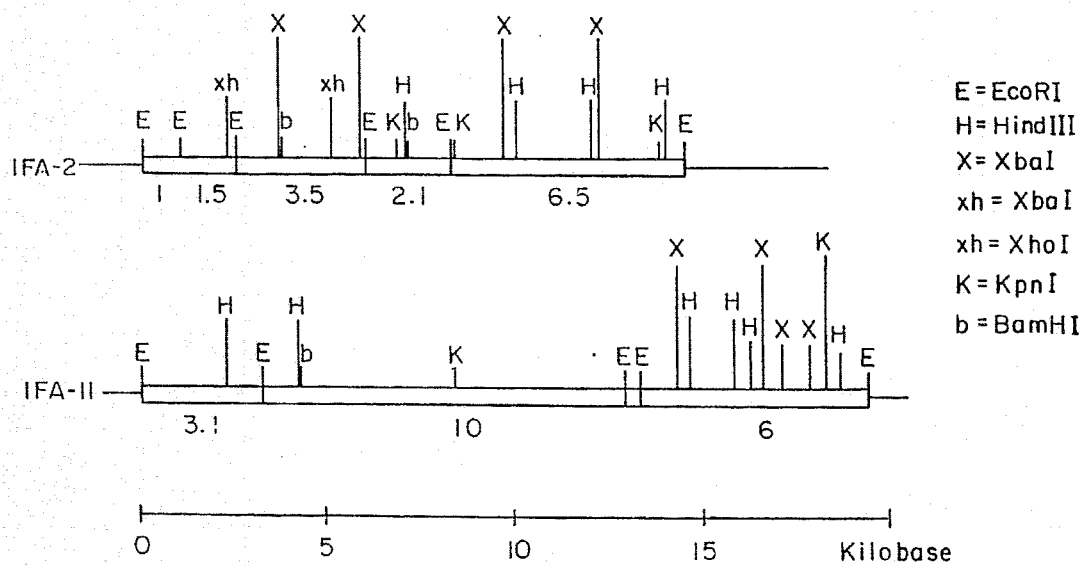

FIG. 8

PRODUCTION OF RECOMBINANT HUMAN INTERFERON-BETA$_2$

CROSS-REFERENCE TO RELATED APPLICATIONS

The present application is a continuation of U.S. application Ser. No. 860,883, filed May 8, 1986, now abandoned, which was a continuation-in-part of prior application Ser. No. 208,925, filed Nov. 20, 1980, now U.S. Pat. No. 5,468,607, the entire contents of which are hereby incorporated by reference.

FIELD OF THE INVENTION

The present invention relates to biologically active human interferon-beta$_2$ (IFN-$\beta_2$) cDNA which codes for IFN-$\beta_2$, genomic clones containing IFN-$\beta_2$ gene, recombinant vectors having an IFN-$\beta_2$ gene and a transcription control promoter, and cell lines capable of producing IFN-$\beta_2$. More particularly, the present invention relates to the above fields in which the human interferon-beta$_2$ is either human interferon-beta$_{2_A}$ (IFN-$\beta_{2_A}$) or human interferon-beta$_{2_B}$ (IFN-$\beta_{2_B}$).

BACKGROUND OF THE INVENTION

Interferon is an important antiviral and antitumor protein produced by the human body. Because of its species specificity, clinical use of interferon requires human interferon. Based on their neutralization by antibodies, three types of interferon have been defined which include interferon-alpha, produced mainly by leucocytes, interferon-beta, produced mainly by fibroblasts, and interferon-gamma, produced mainly by T-lymphocytes.

The major species of interferon produced by human fibroblasts in response to ds RNA is the 20 Kd glycoprotein IFN-$\beta_1$, encoded by a 0.9 kb RNA which is transcribed from an intron-less gene on chromosome 9. However, additional mRNAs which yield IFN activity when microinjected into frog oocytes, have been observed in human fibroblasts induced by poly (rI)(rC) and by a sequential cycloheximide (CHX)-Actinomycin D treatment. While cloning the IFN-$\beta_1$ cDNA, cDNA clones of another co-induced 1.3 kb RNA have been isolated which in reticulocyte lysates code for a 23–26 Kd polypeptide and in oocytes produce human IFN antiviral activity (J. Weissenbach et al. (1980) *Proc. Natl. Acad. Sci. USA* 77:7152–7156; British patent 2063882). Since this activity was inhibited by anti-IFN-$\beta_1$ antibodies, it was designated IFN-$\beta_2$. The protein product of IFN-$\beta_2$ RNA is immunologically distinct from IFN-$\beta_1$, although the biological activities of the two proteins are cross-neutralized by the same antibodies. The IFN-$\beta_2$ 1.3 kb RNA clearly originates from another gene than IFN-$\beta_1$, since IFN-$\beta_2$ RNA is formed in mouse-human hybrids lacking chromosome 9 (U. Nir (1984) Ph.D. Thesis, Weizmann Institute of Science, Rehovot, Israel).

SUMMARY OF THE INVENTION

Accordingly, it is an object of the present invention to confirm the existence of and isolate biologically active human IFN-$\beta_2$.

It is another object of the present invention to enable the production of biologically active human IFN-$\beta_2$.

It is a further object of the present invention to confirm the existence of and isolate biologically active human IFN-$\beta_{2_A}$ and IFN-$\beta_{2_B}$.

It is another object of the present invention to enable the production of biologically active human IFN-$\beta_{2_A}$ and IFN-$\beta_{2_B}$.

It is yet another object of the present invention to isolate cDNA which codes for human IFN-$\beta_2$, and, more particularly, cDNA which codes for human IFN-$\beta_{2_A}$ and cDNA which codes for human IFN-$\beta_{2_B}$.

It is a further object of the present invention to identify genes hybridizing to IFN-$\beta_2$ cDNA.

It is still another object of the present invention to identify genes hybridizing to IFN-$\beta_{2_A}$ cDNA and to IFN-$\beta_{2_B}$ cDNA.

It is yet a further object of the present invention to isolate genomic clones containing an IFN-$\beta_2$ gene, and, more particularly, a genomic clone containing an IFN-$\beta_{2_A}$ gene and a genomic clone containing an IFN-$\beta_{2_B}$ gene.

It is another object of the present invention to provide a recombinant vector containing an IFN-$\beta_2$ gene and a promoter sequence capable of exerting transcription control over the interferon gene.

It is yet another object of the present invention to provide cells which produce biologically active human IFN-$\beta_2$.

It is another object of the present invention to provide such cells which produce substantial quantities of such IFN-$\beta_2$.

It is still another object of the present invention to provide a process for the production of biologically active human IFN-$\beta_2$ by recombinant DNA technology.

It is a further object of the present invention to provide genes which when fused to a strong viral transcriptional promoter and transfected into hamster or mouse cells, produce substantial quantities of biologically active human IFN-$\beta_2$.

In accordance with the present invention, the existence of biologically active human interferon-beta$_2$ (IFN-$\beta_2$) molecules has been confirmed and these molecules are produced by recombinant DNA technology. IFN-$\beta_2$ is a glycoprotein secreted by human fibroblasts which are induced by double-stranded (ds) RNA or viruses to produce interferon. IFN-$\beta_2$ amounts to about 5% of the total IFN activity produced by fibroblasts. The amino acid sequence of IFN-$\beta_2$, which was determined by cDNA sequencing, indicates only about 20% overall homology with that of the other human IFNs produced by such human cells (IFN-$\beta_1$ and IFN-$\alpha$s).

A human cDNA or gene encoding IFN-$\beta_2$ may be cloned in accordance with the present invention and fused to cDNA or to a strong viral transcriptional promoter. Hamster cells transformed by the fused cDNA or gene produce constitutively human-specific interferon activity which inhibits viral replication and cytopathic effect and induces the proteins typical of the biological response of human cells to interferons. A second gene encoding IFN-$\beta_2$ is also disclosed which when isolated and transfected into hamster or mouse cells, produces human-specific IFN activity after induction by ds RNA and cycloheximide. As the IFN produced by both genes have the properties ascribed to IFN-$\beta_2$, but do not have identical amino acid sequences, the proteins produced by the two genes are denominated IFN-$\beta_{2_A}$ and IFN-$\beta_{2_B}$, respectively.

Figure 2:
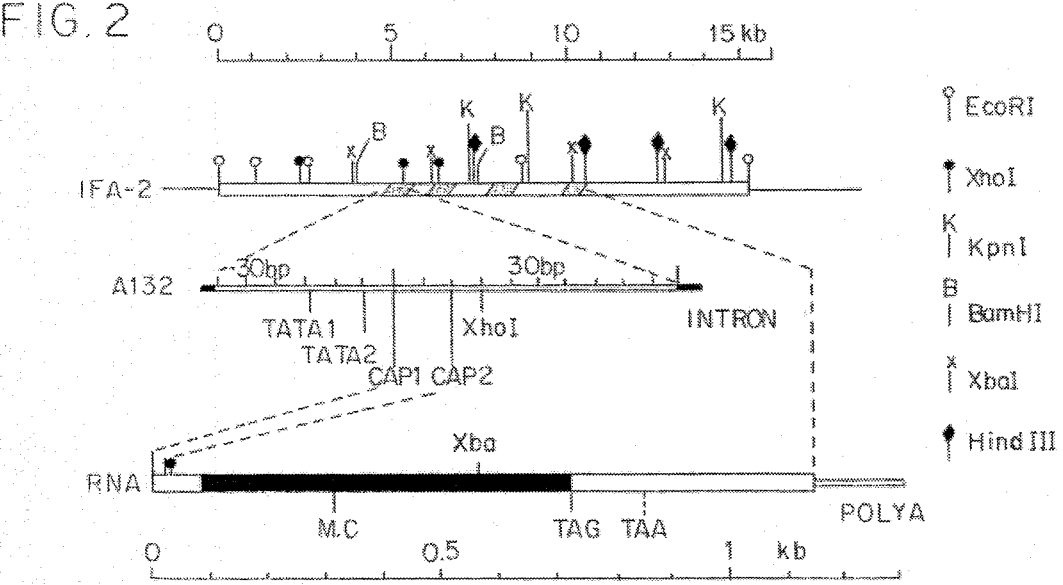

The 5' end sequence was completed from the genomic clone IFA-2 shown in FIG. 2. Numbering begins from the S-1 start of FIGS. 3 and 4. The amino acid sequence of the IFN-$\beta_{2_A}$ protein is deduced.

Figure 1:
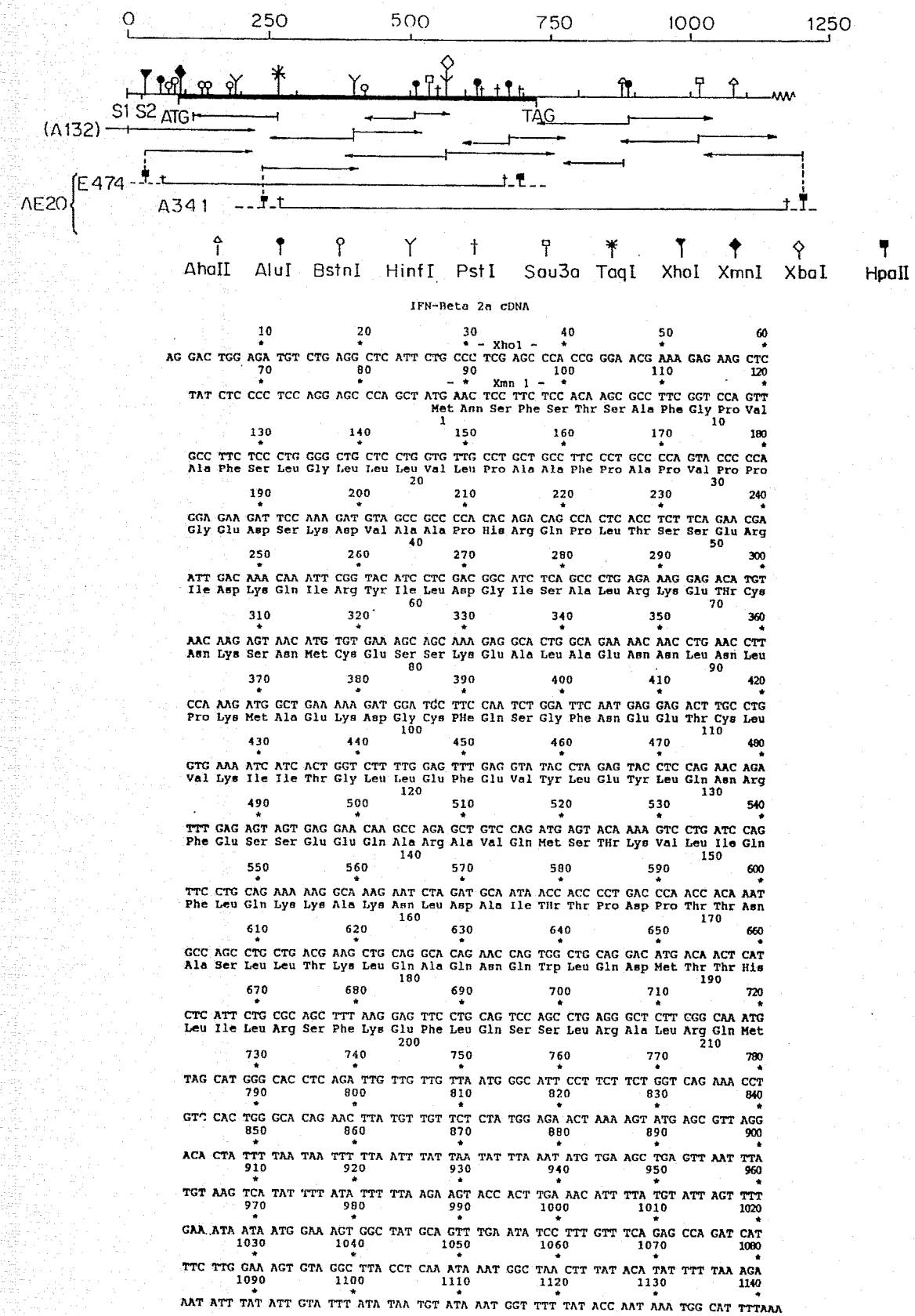
FIG. 1 shows the restriction map, sequencing strategy and nucleotide sequence of IFN-$\beta_{2_A}$ cDNA determined from clone AE20 formed by fusing E474 cDNA and A341 cDNA clones (Weissenbach et al. (1980), supra) by their Xba 1 site.

FIG. 2 shows the structure of genomic clone IFA-2 containing the IFN-$\beta_2$ gene. A132 is a subclone of an EcoRI segment of IFA-2 in pBR322. Shaded areas are gene regions hybridizing to cDNA clones A341 and E474 (Weissenbach et al (1980), supra). The positions of the two RNA starts (cap 1 and 2) and the TATA boxes are shown. In the RNA, the longest open reading frame (ORF) of 212 amino acids (FIG. 1) is shown in black. M.C. indicates a second internal ATG in the same frame. No other long ORF are found in the entire IFN-$\beta_2$ cDNA (FIG. 1).

Figure 3:
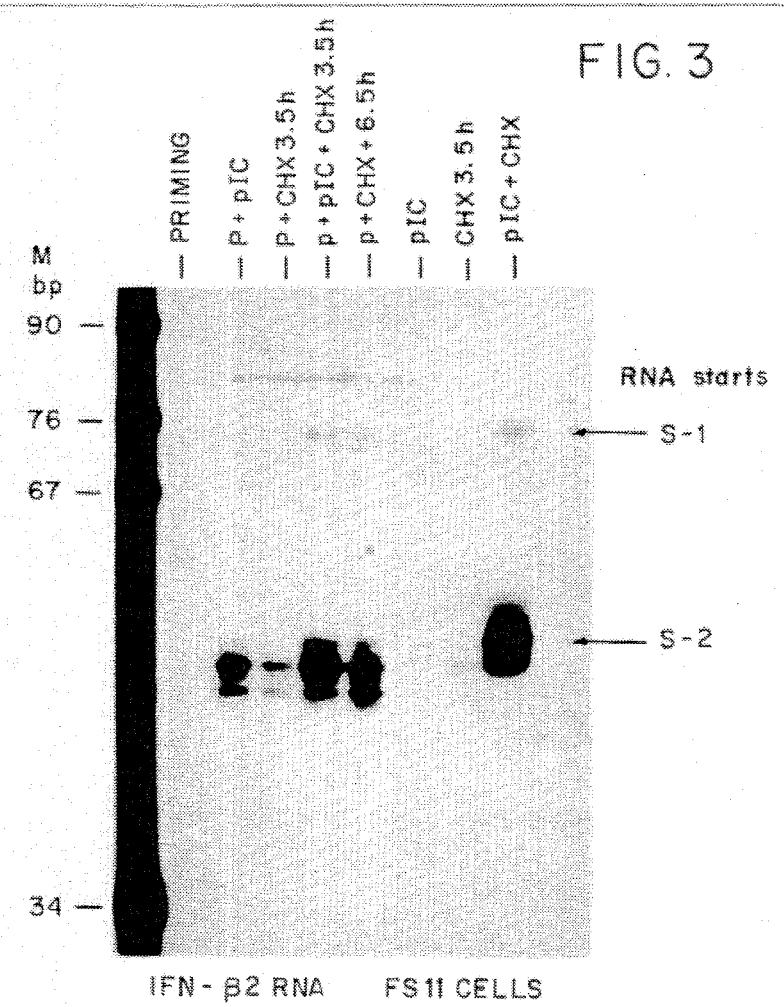

FIG. 3 shows the S1 nuclease analysis of 5' starts in IFN-$\beta_2$ RNA. The DNA probe, a fragment from subclone A132 of IFA-2 gene (FIG. 2) labelled at BstN1 site was hybridized to total RNA from diploid fibroblasts treated (from left to right) by: priming with IFN-$\beta_1$ 200 U/ml 16 hrs, priming and poly (rI)(rC) (pIC) 50 µg/ml 3.5 hours, priming and, cycloheximide (CHX) 50 µg/l ml 3.5 hours, priming and pIC plus CHX 3.5 hours, priming and CHX for 6.5 hours, no priming and pIC 3.5 hrs, same CHX 3.5 hours, same pIC plus CHX 3.5 hours. S-1 and S-2 are the signals generated by the two RNA starts of FIG. 2.

FIG. 4 shows the sequence of the promoter region of the IFA-2 gene encoding IFN-$\beta_{2_A}$. The sequence of part of subclone A132 (FIG. 2) is shown compared to the longest IFN-$\beta_2$ cDNA. S1 and S2 are the two RNA starts determined in FIG. 3. The initiator ATG is marked by X. The first intron starts at intr 1.

FIG. 5 illustrates the fusion of IFN-$\beta_{2_A}$ cDNA to the SV40 early promoter. A plasmid pSVIFA2-II was first constructed by subcloning the 5' Xho$_1$-BamH$_1$ (Xh-B) segment of the IFA-2 gene (from 5.5 kb to 7.5 kb in FIG. 2) fused with a Cla$_1$Xho$_1$ synthetic adaptor of 26 bp (restoring the 5' cDNA sequence), into a Cla$_1$ and Bam H$_1$-cut pBR plasmid. The 3' BamH$_1$-Hind$_{111}$ (B-H) gene segment (from 7.5 kb to 10.5 kb in FIG. 2), subcloned in a Hind$_{111}$, Bam H$_1$ cut pBR plasmid, was excised using the Cla$_1$ site adjacent to Hind$_{111}$ in pBR322 and ligated to the above 5' segment to obtain the complete IFA-2 gene. A pSVE3 vector cut by Hind$_{111}$ as described in Y. Chernajovsky et al, (1984) DNA 3: 294–308, was reclosed with Cla$_1$ linkers (forming pSVCla) and the above IFA-2 gene introduced in the Cla$_1$ site of pSVCla in the same orientation as the SV40 early promoter forming pSVIFA2-II. A plasmid pSVIFA2-I was similarly constructed but the Xho, site of IFA-2 was fused directly to the Cla$_1$, site of pBR before introduction in PSVE3. To obtain the pSVCIF$\beta$2 plasmid containing the IFN-$\beta_{2_A}$ cDNA fused to the SV40 promoter, the above pSVIFA2-II DNA, cut by Xba$_1$, was partially cut by Xmn$_1$ to open the Xmn$_1$ site located 60 bp downstream from the Xho$_1$ site in the IFN-$\beta_2$ cDNA sequence (FIG. 1), and not an Xmn$_1$ site located in the amp gene of the vector. To this construct, the Xmn$_1$-Xba$_1$ segment of IFN-$\beta_2$ cDNA clone AE20 (coordinates 92–566 in FIG. 1) was ligated restoring the complete IFN-$\beta_{2_A}$ cDNA sequence as shown in the Figure. EES is the early-early RNA start of SV40 T-ag gene; ATG is the IFN-$\beta_2$ initiation codon; pA are IFN-$\beta_2$ and SV40 polyadenylation sites, respectively. pSVCIF$\beta$2 DNA was cotransfected with a pDHFR plasmid into CHO-K$_1$ DHFR$^-$ cells as in Y. Chernajovsky et al, (1984), (supra) and clones were tested for human IFN antiviral activity in FS11 cells using Vesicular Stomatitis Virus (VSV). Gene amplification was obtained by selecting CHO clones for methotrexate (MTX)-resistance. Assay of the culture medium of CHO-SVCIF$\beta_2$ B131-5M cells, resistant to 250 nM MTX, is shown in the lower part of the Figure. After VSV cytopathic effect developed, cells in the microplate were stained by methylene blue. Serial two-fold dilutions of the medium are from left to right. By comparison to IFN standard (ST) and non-transfected CHO cells, a titer of 300 U/ml rIFN-$\beta_2$ is calculated.

FIG. 6 shows the results of an assay of (2'–5') oligo A synthetase with poly (rI)(rC)-agarose bound NP40 extracts (M. Revel et al. (1981) *Meth. Enzymol.* 79:149–161) of human FS11 fibroblasts previously exposed 16 hours to medium from a) Cos7 cells two days post-transfection with the pSVIFA2-II DNA described in FIG. 5 (leftmost 4 lanes), b) hamster CHO SI-15 cells stably transformed by the pSVIFA2-I DNA of FIG. 5 (next 4 lanes), c) CHO MEIF-5 cells expressing IFN-$\beta_1$ gene (Y. Chernajovsky et al. (1984), supra) (next 2 lanes), d) CHO cells with DHFR gene only (next lane), e) fresh medium (Non Ind.). The IFN antiviral activity measured per ml of the media added to FS11 cells is indicated. An electrophoresis of phosphatased, 32P-α-ATP labeled (2'–5') oligo A products is shown.

FIG. 7 is a comparison of amino acid sequences between type I human IFNs. Amino acids that are conserved in IFN-$\beta_1$ and the various IFN-αs (shown are αA, αC, replacements in other as excluding αE, and IFN-α class II), are marked by stars over the IFN-$\beta_1$ sequence. Amino acids conserved in IFN-$\beta_2$ are shown above its sequence by stars if conserved in all type I IFNs, or by squares if conserved in some IFNs. IFN-$\beta_{2_A}$ was aligned by comparing hydropathy plots (see text) and numbered from the presumed processing site.

FIG. 8 shows restriction maps of the two different human IFN-$\beta_2$ genes which are expressed in rodent cells. The IFA-11 DNA (IFN-$\beta_{2_B}$ gene) was transfected into either CHO or L cells and expressed IFN-$\beta$ activity after induction (Table 1).

DETAILED DESCRIPTION OF PREFERRED EMBODIMENTS

The existence of interferon beta$_2$ was discovered in the course of attempts to isolate genetic material containing the nucleotide sequence coding for interferon in human fibroblast cells. In this process, fibroblast cells were induced for the production of inducible interferon mRNA with a suitable exogenous factor and then the mRNAs were extracted. At the same time the mRNAs from a non-induced culture of the same host cells were extracted. cDNA probes were synthesized from the mRNAs of both the induced culture and the non-induced control culture using the corresponding mRNAs as templates (induced cDNAs and non-induced cDNAs). Double-stranded cDNAs derived from the mRNA extracted from the induced culture were then synthesized and such cDNAs were inserted in appropriate vectors and transfected into suitable microorganisms. The microorganisms were cultivated under conditions suitable to cause selective development of microorganism colonies of the modified vectors (initial colonies). Duplicate colonies of the initial colonies were formed and the DNAs of both the initial and duplicate colonies were freed in situ. The DNAs of one of the two sets of duplicate colonies were hybridized with the cDNA probes synthesized from the mRNAs extracted from the induced culture and the other of the two sets of duplicate colonies were hybridized with the cDNA probes synthesized from the mRNAs extracted from the non-induced culture. Clones which selectively hybridized with the induced cDNA probes but not with the non-induced cDNA probes were selected and their DNAs recovered. These cloned DNAs were further tested to determine those DNAs capable of hybridizing with mRNA translatable in frog oocytes or reticulocyte-lysates into interferon, which DNAs are essentially those which code for interferon, or contain enough of the sequence coding for interferon to be used to obtain a complete interferon DNA.

During this investigation, it was discovered that two different mRNAs coding for interferon could be isolated from human fibroblast cells after being appropriately induced. Upon glycerol gradient centrifugation the smallest mRNA sediments at 11S and yields by translation in a cell-free system a protein of molecular weight 20,000 which is selectively precipitated by antibodies prepared against one of the interferons that can be purified from these cells. This protein is human interferon-beta$_1$ whose amino acid sequence was partially determined by Knight, E. et al (1980) *Science*, 207, 525–526. The largest mRNA was found to sediment at 14S and yield a protein of molecular weight 23,000 which is precipitated by antibodies against a less purified preparation of fibroblast interferon. This protein is designated human interferon-beta$_2$. cDNA clones hybridizable to mRNA which translates to interferon-beta$_2$ were prepared in such a manner and an IFN-$\beta_2$ cDNA probe was prepared therefrom.

Two such IFN-$\beta_2$ cDNA clones A341 and E474 were found to represent overlapping sequencing and were fused to reconstitute the IFN-$\beta_2$ AE20 cDNA (FIG. 1). The nucleotide sequence of this IFN-$\beta_2$ cDNA was determined and revealed an open reading frame of 212 amino acids predicting a protein of 23,500 daltons. Transcription-translation experiments confirmed that this cDNA encodes such a protein.

From a human gene library of human adult blood cell DNA cloned after partial EcoR1 digestion in γ charon 4A (Y. Mory et al. (1981) *Eur. J. Biochem.* 120:197–202), two genomic clones IFA-2 and IFA-11 hybridizing to such an IFN-$\beta_2$ cDNA probe were isolated. Clone IFA-2 contains a gene with at least 4 exons hybridizing to various segments of the cloned cDNA (FIG. 2). An XhoI site present near the 5' of the AE20 cDNA allowed to map the genomic segment A132 (FIG. 2) which contains the first IFA-2 exon ending 70 bp downstream from this XhoI site. By S1 nuclease analysis using DNA probes labeled at a BstN1 site 40 bp after the XhoI site, it was determined that induced FS11 human fibroblasts contain IFN-$\beta_2$ RNA with two distinct 5' ends S-1 and S-2 separated by 20 nucleotides (FIG. 3). Each of these two starts is preceded in the IFA-2 gene by a potential TATA box at –30 (FIG. 4). RNA ending at S-2 seems to be more abundant than the longer RNA under a variety of induction conditions (FIG. 3). Both RNA 5' ends were also seen with cytoplasmic RNA instead of total cell RNA. Therefore, it is apparent that both RNAs are formed and active in human cells. Both IFN-$\beta_2$ RNAs are induced in human fibroblasts by poly (rI)(rC) and induction is stimulated by IFN priming as in the case of IFN-$\beta_1$ RNA in these cells (U. Nit et al. (1984) *Nucl. Acids Res.* 12:6979–6993). A prolonged (6.5 h) treatment with CHX also induces IFN-$\beta_2$ RNA, but shorter (3.5 h) CHX treatment is effective only with poly (rI)(rC) (FIG. 3). The low induction of IFN-$\beta_2$ RNA by CHX without ds RNA distinguishes this gene from IFN-$\beta_1$.

DNA constructs were made to express the IFA-2 gene under the control of the SV40 early gene promoter. A 4.8 kb segment of IFA-2 DNA was fused through a synthetic oligonucleotide to pSVE3 DNA (Y. Chernajovsky et al. (1984), supra) so that the ATG codon is 150 bp downstream from the SV40 early early RNA start (pSVIFA2-II; see brief description of FIG. 5, supra). After transfection of pSVIFA2-II DNA into Cos7 monkey cells (Y. Gluzman (1981) *Cell* 23:175–182), two RNAs of 1.35 and 2.2 kb were detected in Northern blots by IFN-$\beta_2$ cDNA; these two RNAs would correspond to transcripts ending at the IFN-$\beta_2$ and SV40 polyadenylation sites respectively (FIG. 5). Medium from the Cos7 cells during transient expression of the pSVIFA2-II DNA was assayed for IFN activity by inhibition of the cytopathic effect of VSV on human FS11 and Wish cells as described in D. Novick et al. (1983) *J. Gen. Virol.* 64: 905–910. Antiviral activity could be clearly detected two days after transfection (Table 1). The specific antiviral activity of IFN-$\beta_2$ per unit protein has been estimated to be 30–100 times lower than that of IFN-$\beta_1$ and closer to that of IFN-$\alpha_1$ (5–10×10$^6$ units/mg). The IFN titers observed by transient expression of the IFA-2 gene were as expected, about 3% of those seen with the IFN-$\beta_1$ gene under the same SV40 promoter control (Table 1). Production of IFN-$\beta_2$ activity by pSVIFA2-II DNA cells was further demonstrated by induction of (2'-5') oligo A synthetase (M. Revel et al. (1981), supra) in FS11 cells exposed to the medium of the transfected Cos7 cells (FIG. 6). The induction was dose-dependent and corresponded quantitatively to the antiviral activity.

The IFA-2 gene was also fused to the SV40 early promoter directly at the XhoI site near S-2 (pSVIFA2-I DNA; see brief description of FIG. 5, supra). Hamster CHO-K1 DHFR$^-$ cells were cotransformed with pSVIFA2-I and pSVDHFR (Y. Chernajovsky et al. (1984), supra) DNAs and a stably transformed line SI-15 was isolated. This cell line produces constitutively 10–50 U/ml of IFN antiviral activity measured on human FS11 and Wish cells, while CHO cells transformed only by pSVDHFR produce no human IFN (Table 1). By concentration of the medium from SI-15 cultures, rIFN-$\beta_2$ solutions titrating about 3000 U/ml could regularly be obtained. This rIFN-$\beta_2$ has the properties expected for a human IFN and induces the (2'-5') oligo A synthetase in FS11 cells even at low concentrations of 1 U/ml (FIG. 6). The rIFN-$\beta_2$ constitutively produced by CHO SI-15 cells demonstrated human-specific induction of the mRNAs for (2'-5') oligo A synthetase, C56 and HLA in the presence of cycloheximide, its antiviral activity was neutralized by anti-IFN-$\beta_2$ (but not anti-IFN-$\alpha$ or anti-IFN-$\gamma$) polyclonal and monoclonal antibodies and it acted on mouse-human hybrids only if they contain human chromosome 21 which carries the gene for the type I IFN receptor. These further characterizations of the biological activity of rIFN-$\beta_2$ convincingly demonstrate that it acts directly as an IFN and is not an inducer of IFN-$\beta_1$.

Improved yields of rIFN-$\beta_2$ were obtained with DNA constructs containing the IFN-$\beta_2$ cDNA sequence fused to the SV40 early promoter (pSVCIF$\beta$2 shown in FIG. 5), when this DNA, cotransfected with pSVDHFR into CHO cells as above, was amplified by selecting cells resistant to increasing concentrations of methotrexate. Without amplification, the pSVCIF$\beta$2-transformed CHO cells (e.g., clone B-131) produced levels of IFN-$\beta_2$ activity similar to those produced by the SI-15 cells (Table 2). However, after selection for resistance to methotrexate, higher yields were obtained with up to 800 U/ml (Table 2).

From such clones it was possible to immuno-precipitate the IFN-$\beta_2$ protein secreted into the culture medium and, if the cells had been labeled by $^{35}$S-methionine, to analyze the IFN-$\beta_2$ protein by dodecyl sulfate polyacrylamide gel electrophoresis. The size of the secreted rIFN-$\beta_2$ was found to be 21,000 daltons. Indeed, experiments have shown that the 23–26 Kd primary translation product of IFN-$\beta_2$ RNA in reticulocyte lysates is processed in vitro by dog pancreatic membranes into a shortened 21 Kd protein, and that induced human fibroblasts produce a 21 Kd protein which is immunologically similar to the IFN-$\beta_2$ RNA 26 Kd product, but distinct from IFN-$\beta_1$. The N-terminus of the mature IFN-$\beta_2$ 21 Kd protein has not been determined and two potential glycosylation sites are present in the IFN-$\beta_2$ sequence (FIG. 1), making it difficult to calculate the size of the region removed by processing. However, the decrease in size indicates that this processed region is longer than that in IFN-$\beta_1$ whose size increases by maturation (W. Degrave et al. (1981) *Gene* 10: 11–15). A hydropathy plot of the IFN-$\beta_2$ 26 Kd polypeptide has shown that there is a marked similarity between hydrophobic and hydrophilic regions of IFN-$\beta_2$ and of mature IFN-$\beta_1$, when the two proteins are aligned by their C-termini. The same alignment also reveals conservation in the amino acid sequence of IFN-$\beta_2$ with those of the other type I human IFNs (FIG. 7). Between all the known IFN-$\alpha$s and $\beta_1$ sequences, there are 38 amino acids which are conserved (marked by stars in FIG. 7). When IFN-$\beta_2$ is aligned as above, 18 of these 38 amino acids common to all type I human IFNs can be seen to be conserved (FIG. 7). There is an overall homology of about 20% between IFN-$\beta_2$ and the other type I IFNs.

Although the sequence homology between IFN-$\beta_1$ and $\beta_2$ is low, the cross-neutralization of the anti-viral activities of IFN-$\beta_1$ and IFN-$\beta_2$ by the same antibodies, including a monoclonal anti-IFN-$\beta_1$ (D. Novick et al. (1983), supra), could result from some conserved structure in the active site of IFN-$\beta$. IFN-$\beta_2$ activity is not neutralized by anti-IFN-$\alpha$ or $\gamma$ antibodies, justifying its designation as a $\beta$-type IFN. The genes encoding IFN-$\beta_2$ are not on chromosome 9 (U. Nir (1984), supra) and differ from the type I IFN genes in the chromosome 9 cluster by the presence of introns. The IFA-2 gene was determined to be on chromosome 7 (Sehgal P. B. et al. (1986) *Proc. Natl. Acad. Sci. USA*, in press). The amino acid sequence homology detected is compatible with the notion that the IFN-$\beta_2$ genes are related to the ancestral gene which gave rise to the type I IFN gene cluster.

The second genomic DNA clone IFA-11 hybridizing with the IFN-$\beta_2$ cDNA has a restriction map which differs from that of IFA-2 (FIG. 8). Transcript mapping and sequencing showed that the 3' exon of IFA-2 and IFA-11 (Xba1-HindIII segment) are identical (99% sequence homology), while there was no cross-hybridization under stringent conditions between more 5' exons. The IFA-11 genomic clone (19 Kb) was transfected into L-TK$^-$ cells together with a HSV-TK gene (F. Colbere-Garapin et al. (1981) *J. Mol. Biol.* 150:1–14) and stable transformants were isolated. Table 1 shows that L cell clone LI-39 containing the human IFA-11 gene, produces human IFN activity when induced by poly (rI)(rC) and cycloheximide, while L-TK$^+$ cells produced no such activity. A CHO clone 1C40 containing the IFA-11 gene also produced human IFN activity (Table 1). No activity was seen in non-induced LI-39 or 1C40 cells. The IFN activity obtained with IFA-11 transformants after induction was significantly higher than with the IFA-2 gene. The rIFN-$\beta_{2_B}$ produced by expression of the IFA-11 gene was neutralized with anti-IFN-$\beta_1$ similarly to the IFA-2 gene product. IFA-11 specific DNA probes hybridized to RNA from induced human fibroblasts similarly to IFA-2 DNA probes, indicating that both genes are active in human cells.

TABLE 1

Antiviral Activity of rIFN-$\beta_2$* Produced in Transfected Mammalian Cells

| | |
|---|---|
| I. | IFA-2 GENE |
| A. | Constitutive expression in CHO cells |
| | pSVIFA2-I SI-15 cells: 10–50 U/ml** |
| | (control CHO cells: 0) |
| B. | Transient expression in Cos-7 cells |
| | pSVIFA2-II DNA: 15 U/ml |
| | (control IFN-B$_1$ pSVEIF DNA: 500 U/ml) |
| II. | IFA-11 GENE |
| A. | Induced expression*** in CHO cells |
| | Clone 1C40: 400–500 U/ml |
| | (control CHO cells: 100 U/ml) |
| B. | Induced expression in L cells |
| | Clone L1-39: 250 U/ml |
| | (control L-TK$^+$ cells: <4 U/ml) |

*Assay with VSV in FS11 and WISH cells. Neutralized by anti IFN-$\beta_1$.
**3000 U/ml after concentration.
***Induction with poly IC and cycloheximide for 10 hrs. Harvest at 28 hrs.

TABLE 2

Antiviral Activity Of Human r-IFN-$\beta_{2_A}$ Produced in Hamster Cells Transfected and Amplified with IFN-$\beta_{2_A}$ cDNA

| CHO-SVCIF$\beta_2$ | CLONE | Human IFN activity* U/ml |
|---|---|---|
| B-131 | (0 MTX)** | 64 |
| B-131-5M | (250 nM MTX)** | 300 |
| B-131-10M | (500 nM MTX) | 800 |

*Medium from cultures was collected every 24 hours and assayed with VSV in FS11 human cells. The activity was neutralized by anti-IFN-$\beta_1$, but not anti-IFN-$\alpha$ or anti-IFN-$\gamma$.
**Cultures were selected for resistance to indicated concentrations of methotrexate.

The function of the IFN-$\beta_2$ genes seems to result from their expression under conditions in which other IFN genes are not expressed. Fibroblasts exposed to Tumor Necrosis Factor (TNF) or to the lymphokine IL-1 produce the IFN-$\beta_2$ protein. Others have found that neutralization of IFN-$\beta$ by antibodies results in a stimulation of cell proliferation (Kohase M. et al. (1986) *Cell*, in press; Resnitzky D. et al. (1986) *Cell*, in press), suggesting that the IFN-$\beta_2$ acts to limit cell growth in response to growth factors. Supporting this conclusion is the fact that RNA hybridizing to IFN-$\beta_2$ cDNA was recently detected in peripheral blood mononuclear cells induced by mitogens such as PHA along with IFN-$\gamma$ mRNA. It has also been reported that an IL-1 like lymphokine strongly induces RNA hybridizing to IFN-$\beta_2$ cDNA in diploid fibroblasts and other human cell lines (Content, J., et al (1985) *Eur. J. Biochem.* 152:253–7). The promoter region of the IFA-2 genes seems to contain two TATA boxes and two RNA starts (FIGS. 1 and 3). This IFN-$\beta_2$ promoter was shown to respond to either poly (rI)(rC) or to cycloheximide (Y. Chernajovsky et al. (1984), supra). In vivo, the two IFN-$\beta_2$ gene promoters may be activated by different inducers (ds RNA, protein synthesis inhibitors, IL-1, PHA). A variety of cells have been found to produce autocrine IFN-$\beta$ in low amounts during growth arrest and differentiation (Revel, M. et al (1983) *Interferon* 5 pp. 205–239, Acad. Press, London). IFN-$\beta_2$ may belong to the same group of minor IFN species produced by cells to auto-regulate their growth while the classical type I IFNs are probably more specifically involved in the response to viral infections.

Clones IFA-2, IFA-11 and CHO-SVCIF$\beta_2$ B-131-10M have each been deposited at the Institut Pasteur, Collection Nationale de Cultures de Microorganismes, 25, Rue de Docteur Roux, 75724 Paris, Cedex 15, France. Clone IFA-2 has been given accession No. I-1087, clone IFA-11 has been given accession No. I-1086 and clone CHO-SVCIFβ2 B-131-10M has been given accession No. I-1084.

To the extent that it may be deemed necessary in order to complete the disclosure in this case, all of the subject matter of each of the publications referred to and cited hereinabove are hereby incorporated herein by reference.

It will be obvious to those skilled in the art, that various other changes and modifications may be made without departing from the scope of the invention and the invention is not to be considered limited to what is shown in the drawings and described in the specification.

We claim:

1. A recombinant vector comprising a DNA sequence which codes for human interferon-beta$_{2_A}$ and further comprising a regulatory region positioned in a way that expression of the human interferon beta$_{2_A}$ is possible.

2. A recombinant vector in accordance with claim 1, wherein said regulatory region is an SV40 early promoter sequence.

3. A cell comprising a transformed cell transformed by a recombinant vector in accordance with claim 2, or progeny thereof containing the genetic information imparted by said vector.

4. A cell comprising a transformed cell, transformed by a recombinant vector in accordance with claim 1, or progeny thereof containing the genetic information imparted by said vector.

5. A process for the production of interferon-$\beta_{2A}$ (IFN-$\beta_{2A}$) comprising culturing cells in accordance with claim 4 under conditions sufficient for the expression of IFN-$\beta_{2A}$.

6. A recombinant vector in accordance with claim 1 wherein said DNA sequence is a genomic DNA sequence containing the human interferon beta$_{2_A}$ gene.

7. A recombinant vector in accordance with claim 6, consisting essentially of pSVIFA2-I.

8. A recombinant vector in accordance with claim 6, consisting essentially of pSVIFA2-II.

9. A cell comprising a transformed cell transformed by a recombinant vector in accordance with claim 6, or progeny thereof containing the genetic information imparted by said vector.

10. A cell in accordance with claim 9, wherein said cell is a CHO cell.

11. A cell in accordance with claim 9, wherein said cell is an L-TK cell.

12. A cell in accordance with claim 9, wherein said cell is eukaryotic.

13. A cell in accordance with claim 12, wherein said cell is a hamster cell.

14. A process for the production of interferon-beta$_{2_A}$ comprising culturing cells in accordance with claim 12 under conditions sufficient for the expression of interferon-beta$_{2_A}$.

15. A recombinant vector in accordance with claim 1 wherein said DNA sequence is a cDNA which codes for human interferon-beta$_{2_A}$.

16. A cell comprising a transformed cell transformed by a recombinant vector in accordance with claim 15, or progeny thereof containing the genetic information imparted by said vector.

17. A cell in accordance with claim 16, comprising a bacterial cell.

18. A process for the production of interferon-beta$_{2_A}$ comprising culturing cells in accordance with claim 17 under conditions sufficient for the expression of interferon-beta$_{2_A}$.

19. A recombinant vector in accordance with claim 15 wherein said interferon-beta$_{2_A}$ cDNA is the interferon-beta$_{2_A}$ cDNA as shown in FIG. 1.

20. A recombinant vector in accordance with claim 19, consisting essentially of pSVCIFβ2.

21. A cell comprising a transformed cell transformed by a recombinant vector in accordance with claim 19, or progeny thereof containing the genetic information imparted by said vector.

22. A non-human cell, containing a human gene consisting essentially of the human interferon-$\beta_{2A}$ gene.

23. A cell in accordance with claim 22, wherein said human interferon-$\beta_{2A}$ gene is the IFA-2 gene.

24. A cell in accordance with claim 22, capable of producing a polypeptide having the amino acid sequence of human interferon-$\beta_{2A}$.

* * * * *